(12) United States Patent
Moriura et al.

(10) Patent No.: US 8,163,124 B2
(45) Date of Patent: Apr. 24, 2012

(54) METHOD AND DEVICE FOR PRODUCING SHEET-LIKE BODY AND METHOD FOR PRODUCING DISPOSABLE ABSORBENT ARTICLE USING THE SHEET-LIKE BODY

(75) Inventors: Osamu Moriura, Mino-cho (JP); Kazuya Maruhata, Tsurugi-cho (JP)

(73) Assignee: Livedo Corporation, Ehime (JP)

( * ) Notice: Subject to any disclaimer, the term of this patent is extended or adjusted under 35 U.S.C. 154(b) by 370 days.

(21) Appl. No.: 10/566,533

(22) PCT Filed: Jul. 30, 2004

(86) PCT No.: PCT/JP2004/011298
§ 371 (c)(1),
(2), (4) Date: Jan. 30, 2006

(87) PCT Pub. No.: WO2005/011548
PCT Pub. Date: Feb. 10, 2005

(65) Prior Publication Data
US 2006/0278335 A1  Dec. 14, 2006

(30) Foreign Application Priority Data

Jul. 31, 2003  (JP) ................................. 2003-284129
Jan. 19, 2004  (JP) ................................. 2004-010380

(51) Int. Cl.
*B32B 5/30* (2006.01)
*A61F 13/535* (2006.01)
(52) U.S. Cl. ........................................ 156/276; 604/368
(58) Field of Classification Search .................... 604/368
See application file for complete search history.

(56) References Cited

U.S. PATENT DOCUMENTS

| 3,426,505 | A |   | 2/1969  | Cloud |   |
|---|---|---|---|---|---|
| 4,232,674 | A | * | 11/1980 | Melican | 604/369 |
| 4,507,173 | A |   | 3/1985  | Klowak et al. |   |
| 4,571,924 | A |   | 2/1986  | Bahrani |   |
| 4,720,321 | A |   | 1/1988  | Smith |   |
| 4,851,069 | A | * | 7/1989  | Packard et al. | 156/284 |
| 4,994,053 | A | * | 2/1991  | Lang | 604/367 |
| 5,237,945 | A | * | 8/1993  | White | 112/420 |
| 5,482,761 | A |   | 1/1996  | Palumbo et al. |   |
| 5,868,895 | A |   | 2/1999  | Inoue |   |

(Continued)

FOREIGN PATENT DOCUMENTS

JP  2000-107221  4/2000

(Continued)

OTHER PUBLICATIONS

Supplementary European Search Report for European Patent App. No. 04748269.0 (Nov. 21, 2011).

(Continued)

*Primary Examiner* — Michael Tolin
(74) *Attorney, Agent, or Firm* — Cermak Nakajima LLP; Tomoko Nakajima (57) ABSTRACT

A method for manufacturing a sheet-shaped body in which a powder particle layer is sandwiched between a base sheet to which a bonding agent is applied and a covering sheet so as to be bonded into an integral body, is provided with the steps of: shifting the base sheet, the powder particle layer and the covering sheet, with each of the sheets and the layer being held on the respective roller face, and after the powder particle layer has been transferred onto the base sheet, bonding the base sheet, the powder particle layer and the covering sheet into an integral form. Thus, the powder particle layer can be fixed to a predetermined position in a stable manner.

12 Claims, 7 Drawing Sheets

U.S. PATENT DOCUMENTS

| | | | |
|---|---|---|---|
| 5,925,439 A * | 7/1999 | Haubach | 428/178 |
| 6,287,706 B1 | 9/2001 | Simpson et al. | |
| 7,241,358 B2 | 7/2007 | Gerlach | |
| 7,284,973 B2 | 10/2007 | van Esbroeck et al. | |
| 2002/0115969 A1 | 8/2002 | Maeda et al. | |
| 2003/0084767 A1 | 5/2003 | Tanaka et al. | |
| 2003/0201052 A1 | 10/2003 | Koslow | |

FOREIGN PATENT DOCUMENTS

| | | |
|---|---|---|
| JP | 2002-345883 | 12/2002 |
| JP | 2003-199790 | 7/2003 |
| JP | 2003-1999790 | 7/2003 |
| WO | WO-01/89439 | 11/2001 |
| WO | WO-03/000163 | 1/2003 |

OTHER PUBLICATIONS

Office Action from co-pending U.S. Appl. No. 12/231,970 (Dec. 22, 2011).

Advisory Action from co-pending U.S. Appl. No. 12/231,970 (Feb. 24, 2012).

* cited by examiner

METHOD AND DEVICE FOR PRODUCING SHEET-LIKE BODY AND METHOD FOR PRODUCING DISPOSABLE ABSORBENT ARTICLE USING THE SHEET-LIKE BODY

TECHNICAL FIELD

This invention relates to a method and a device for manufacturing a sheet-shaped body, and a method for manufacturing a disposable absorbent article using the sheet-shaped body.

BACKGROUND ART

Conventionally, a device, which manufactures a sheet-shaped absorbent body in which a highly absorbent resin particle layer is sandwiched between a base sheet to which a bonding agent is applied and a covering sheet so as to be bonded into an integral body, has been proposed (for example, see International Application Laid-Open WO01/89439).

In addition, a continuous manufacturing method of a shorts-type disposable diaper has also been proposed (for example, Japanese Patent Application Laid-Open No. 2002-345883).

In the Patent Document 1, highly absorbent resin particles are naturally dropped onto the base sheet to which an adhesive has been applied to be formed into a layer, and the base sheet, the highly absorbent resin particle layer and the covering sheet are bonded into an integral form so that a sheet-shaped absorbent body is manufactured.

However, there has been such a problem that, when naturally dropping the highly absorbent resin particles, the highly absorbent resin particles bounce on the base sheet, and it becomes difficult to obtain a sheet-shaped absorbent body in which the highly absorbent resin particle layer is stably fixed onto a predetermined position.

The present invention has been made in order to solve the above-mentioned problem, and its objective is to provide a method and a device for manufacturing a sheet-shaped body that is capable of stably fixing a powder particle layer at a predetermined position, and a manufacturing method of a disposable absorbent article using the sheet-shaped body.

DISCLOSURE OF THE INVENTION

In order to solve the above-mentioned problem, the present invention relates to a method that manufactures a sheet-shaped body in which a powder particle layer is sandwiched between a base sheet to which a bonding agent is applied and a covering sheet so as to be bonded into an integral body, is provided with the steps of:

shifting the base sheet, the powder particle layer and the covering sheet, with each of the sheets and the layer being held on the respective roller faces, and after the powder particle layer has been transferred onto the base sheet, bonding the base sheet, the powder particle layer and the covering sheet into an integral form.

In accordance with this invention, since the powder particle layer is transferred onto the base sheet while being shifted in the held state on the respective roller faces, it is possible to prevent the powder particles from bouncing, which makes this method different from the system in which powder particles are allowed to naturally drop to form a layer; therefore, it becomes possible to prepare the sheet-shaped body in which the powder particle layer is stably fixed onto a predetermined position.

In addition, since the base sheet, the powder particle layer and the covering sheet are bonded into an integral form while being shifted, with each of the sheets and the layer being held on the respective roller faces, it is possible to easily control the shifting speeds and the bonding processes of the respective materials, and also to carry out the processes even in a narrow space. Therefore, in the case when the powder particle layer is prepared as a highly absorbent resin particle layer, the manufacturing method of a sheet-shaped body is easily assembled into a continuous manufacturing line of a disposal absorbent article.

BRIEF DESCRIPTION OF THE DRAWINGS

FIG. 2($a$) is a side view showing the manufacturing device of a sheet-shaped absorbent body and FIG. 2($b$) is a side view showing an essential portion of the manufacturing device of a sheet-shaped absorbent body having a protective plate member.

FIG. 3($a$) is a front view that shows a temporary receiving roller; FIG. 3($b$) is an enlarged side sectional view that shows an essential portion of the temporary receiving roller; FIG. 3($c$) is a plan view that shows a base sheet immediately after a highly absorbent resin particle layer has been transferred thereon; FIG. 3($d$) is a side view of FIG. 3($c$); FIG. 3($e$) is a plan view that shows the base sheet immediately after the highly absorbent resin particle layer has been linearly aligned; and FIG. 3($f$) is a side view of FIG. 3($e$).

FIGS. 4($a$) to 4($h$) are plan views of base sheets on which highly absorbent resin particle layers having patterns of respective types have been transferred.

FIGS. 5($a$) and 5($b$) show a sheet-shaped absorbent body; FIG. 5($a$) is a plan view; and FIG. 5($b$) is an enlarged sectional view taken along line D-D of FIG. 5($a$).

FIGS. 6($a$) and 6($b$) show a disposable absorbent article; FIG. 6($a$) is a plan view; and FIG. 6($b$) is an enlarged sectional view taken along line E-E of FIG. 6($a$).

FIG. 7($a$) is a side view of a manufacturing device of a sheet-shaped absorbent body constituted by a plurality of layers, and FIG. 7($b$) is a sectional view showing the sheet-shaped absorbent body constituted by a plurality of layers.

BEST MODE FOR CARRYING OUT THE INVENTION

The invention relates to a manufacturing method of a sheet-shaped body which includes the step of transferring the powder particle layer onto the base sheet, with the powder particle layer being shifted in the same direction as the base sheet. In accordance with the invention, since the powder particle layer is transferred onto the base sheet while being shifted in the same direction as the base sheet, it becomes possible to smoothly transfer the powder particle layer, with the powder particle layer being kept free from bouncing.

The invention relates to a manufacturing method of a sheet-shaped body which is designed so that the shifting speeds of the base sheet, the powder particle layer and the covering sheet are set to the same speed or the shifting speed of the powder particle layer is made slower. In accordance with the invention, since the base sheet, the powder particle layer and the covering sheet are shifted at the same speed or since the powder particle layer is shifted at a slower speed; therefore, it becomes difficult for the powder particle layer to flow at the same speed so that the sheet-shaped body in which the powder particle layer is stably fixed at a predetermined position can be obtained.

The invention is designed so that the process for transferring the powder particle layer on the base sheet and the process for bonding the covering sheet are carried out on the same roller face. In accordance with the invention, since the covering sheet is bonded in a short time after the powder particle layer has been transferred onto the base sheet, the powder particle layer can be enclosed between two sheets quickly so that the sheet-shaped body in which the powder particle layer is stably fixed at a predetermined position can be obtained. In addition, the processes can be carried out even in a narrow space; therefore, even in the case when the powder particle layer is prepared as a highly absorbent resin particle layer, the manufacturing device for the sheet-shaped body is easily assembled into a continuous manufacturing line of a disposable absorbent article.

In accordance with the invention, since the powder particle layer is made of a highly absorbent resin particle layer, the sheet-shaped body is constituted by a sheet-shaped absorbent body.

Here, the powder particle body refers to a solid substance having a grain size (dimension) in which at least one powder particle body is allowed to enter a square cubic body having 3 mm square without a change in its shape. With respect to the shape thereof, not particularly limited, any shape, such as a thin film shape and a fiber shape, may be used as long as the size is set as described above. In addition, with respect to the fluidity index, the substance is set to a value of 40 or more. The substance needs to have an electrically and chemically stable state in which none of adhesion, bonding, aggregation and cross-linking occur between the particles as well as between the particles and substances derived from the particle transferring process, due to an intermolecular force, a magnetic force, a chemical reaction and the like.

With respect to the powder particle body, for example, a highly absorbent resin particle layer for use in a sheet-shaped absorbent body is used in the present embodiment; however, by using the following materials as the powder particle body, the resulting sheet-shaped body can be used for other applications.

The material for the powder particle body include, for example, asphalt, aluminum, aluminum chloride, potassium chloride, calcium chloride, iron pyrite, activated charcoal, clay (kaolin), synthetic wax, acetic acid fiber elements, zinc oxide, iron oxide, CMC acid, salts, barite, sodium bicarbonate, ammonium nitrate, sirasu balloons, magnesium hydroxide, barium stearate, sands, zeolite, sodium sesquicarbonate, limestone, plaster, talc, tungsten carbide, zinc carbonate, potassium carbonate, starch, toner, lead, urine, malt, sodium pyrophosphate, phosphate rock, powdered aluminum oxide, borax, fluorite, bauxite, polyethylene pellets, polystyrene, polyvinyl chloride, mirabilite, anthracite, wood powder, calcined plaster, oil rock, ammonium sulfate, sodium sulfate, calcium dihydrogen phosphate, calcium hydrogen phosphate, tricalcium phosphate, sodium dihydrogen phosphate, disodium hydrogen phosphate and trisodium phosphate, and, these material may be properly selected accordingly depending on the applications. For example, the sheet-shaped body using activated charcoal or zeolite as the powder particle body is applied as a deodorant sheet used for removing offensive stenches of excrements from human bodies and animals. In addition, the sheet-shaped body using limestone as the powder particle body can be buried in soils of rice fields or other fields so as to serve as a fertilizer sheet.

The invention, which relates to a device for manufacturing a sheet-shaped body in which a powder particle layer is sandwiched between a base sheet to which a bonding agent is applied and a covering sheet so as to be bonded into an integral body, is provided with:

a receiving and transferring roller that shifts the base sheet with the base sheet being held on its roller face, a temporary receiving roller that transfers the powder particle layer onto the base sheet, while shifting the powder particle layer, with the powder particle layer being held on its roller face, and a contact-bond fixing roller that bonds the base sheet, the powder particle layer and the covering sheet into an integral form, while shifting the covering sheet with the covering sheet being held on its roller face. In accordance with the invention, since the powder particle layer is transferred onto the base sheet while being shifted in the held state on the roller face, it is possible to prevent the powder particles from bouncing, which makes this device different from the system in which powder particles are allowed to naturally drop to form a layer; therefore, it becomes possible to prepare a sheet-shaped absorbent body in which the powder particle layer is stably fixed onto a predetermined position.

In addition, since the base sheet, the powder particle layer and the covering sheet are bonded into an integral form while being shifted, with each of the sheets and the layer being kept contact with the respective roller faces, it is possible to easily control the shifting speeds and the bonding processes of the respective materials, and also to carry out the processes even in a narrow space. Therefore, in the case when the powder particle layer is prepared as a highly absorbent resin particle layer, the manufacturing device of the sheet-shaped body is easily assembled into a continuous manufacturing line of a disposable absorbent article.

The invention, which relates to the device, has a structure in which: the surface peripheral velocities of the receiving and transferring roller, the temporary receiving roller and the contact-bond fixing roller are set to the same speed, or the surface peripheral velocity of the temporary receiving roller is set to be slower. In accordance with the invention, since the surface peripheral velocities of the receiving and transferring roller, the temporary receiving roller and the contact-bond fixing roller are set to the same speed, or since the surface peripheral velocity of the temporary receiving roller is set to be slower, it becomes difficult for the powder particle layer to flow at the same speed so that the sheet-shaped body in which the powder particle layer is stably fixed at a predetermined position can be obtained, and since the respective materials, which are shifted in the held state on the respective rollers, are allowed to shift at the same peripheral velocity, it becomes possible to easily carry out the controlling process.

The invention, which relates to the device, has a structure in which concave grooves that receive the powder particle layer and shifts the powder particle layer while being held in a layer form are formed on the roller face of the temporary receiving roller. In accordance with the invention, since the powder particle layer, which is received by the concave grooves and held in a layer form, is transferred onto the base sheet, it becomes possible to prevent the powder particles from bouncing, which makes this structure different from the system in which powder particles are allowed to naturally drop to form a layer; therefore, it becomes possible to prepare a sheet-shaped body in which the powder particle layer is stably fixed onto a predetermined position. Here, since the concave grooves hold the powder particle layers individually, it is possible to prevent the powder particles from being spilled from the concave grooves, even when the concave grooves are directed laterally or upside down following the rotation of the temporary receiving roller, and consequently to prevent the powder particles from contaminating around the device.

The invention, which relates to the device, has a structure in which a guide member used for maintaining the powder particle layer is installed therein in a manner so as to face the roller face of the temporary receiving roller. In accordance with the invention, the receiving openings of the concave grooves are sealed with the guide member so that the powder particle layer can be transferred onto the base sheet in a state in which the powder particle layer is enclosed into the concave grooves; therefore, it becomes possible to prevent the powder particles from bouncing, which makes this structure different from the system in which powder particles are allowed to naturally drop to form a layer, and consequently to prepare a sheet-shaped body in which the powder particle layer is stably fixed onto a predetermined position. In addition, it is possible to prevent the powder particles from being spilled from the concave grooves, and consequently to prevent the powder particles from contaminating around the device.

The invention, which relates to the device, has a structure in which at least one of the contact-bond fixing roller and the receiving and transferring roller is a heat roller. In accordance with the invention, a partially fusing process between the sheets caused by heat can be carried out, and it becomes possible to eliminate the necessity of installing a heat roller separately, and consequently to make the device space compacter as well as making the device more easily controlled; therefore, in the case when the powder particle layer is prepared as a highly absorbent resin particle layer, the manufacturing device of the sheet-shaped body is easily assembled into a continuous manufacturing line of a disposable absorbent article.

The invention, which relates to the device, has a structure in which a press contact roller which presses the covering sheet to be in contact with the base sheet on the receiving and transferring roller is installed before the contact-bond fixing roller. In accordance with the invention, immediately after the powder particle layer has been transferred on the base sheet, the base sheet is covered with the covering sheet that is made in press-contact thereto by the press contact roller; therefore, the powder particle layer is prevented from flowing so that a sheet-shaped body in which the powder particle layer is stably fixed at a predetermined position can be obtained.

The invention, which relates to the device, has a structure in which a protective plate member, which prevents the powder particle layer from flowing, is attached to the receiving and transferring roller. In accordance with the invention, it is possible to prevent the powder particle layer from flowing by the protective plate member during a period from the transfer of the powder particle layer onto the base sheet until the covering sheet has been placed and press-secured thereon by the contact-bond fixing roller; therefore, it becomes possible to obtain a sheet-shaped body in which the powder particle layer is stably fixed at a predetermined position.

The invention of claim 13, which relates to the device, features that the distance between the surface of the receiving and transferring roller and the protective plate member is set in a range from 0.5 to 5 mm. In accordance with the invention, since the distance between the surface of the receiving and transferring roller and the protective plate member is set in a range from 0.5 to 5 mm, it becomes possible to positively prevent the powder particle layer from flowing.

The invention, which relates to the device, features that the powder particle layer is a highly water-absorbent resin particle layer. In accordance with the invention, since the powder particle layer is prepared as a highly water-absorbent resin particle layer, the sheet-shaped body is obtained as a sheet-shaped absorbent body. Here, the grain size, kinds and the like of the powder particle layer are the same as those explained in the invention.

The invention features that the sheet-shaped body is sandwiched between a liquid-permeable top sheet and a liquid-impermeable back sheet to be bonded into an integral form so that a disposable absorbent article is produced. In accordance with the invention, it is possible to produce a disposable absorbent article having a sheet-shaped absorbent body in which the highly water-absorbent resin particle layer is stably fixed at a predetermined position.

Referring to Figures, the following description will discuss the preferred mode for carrying out the invention in detail.

EXAMPLE 1

Figure 1:
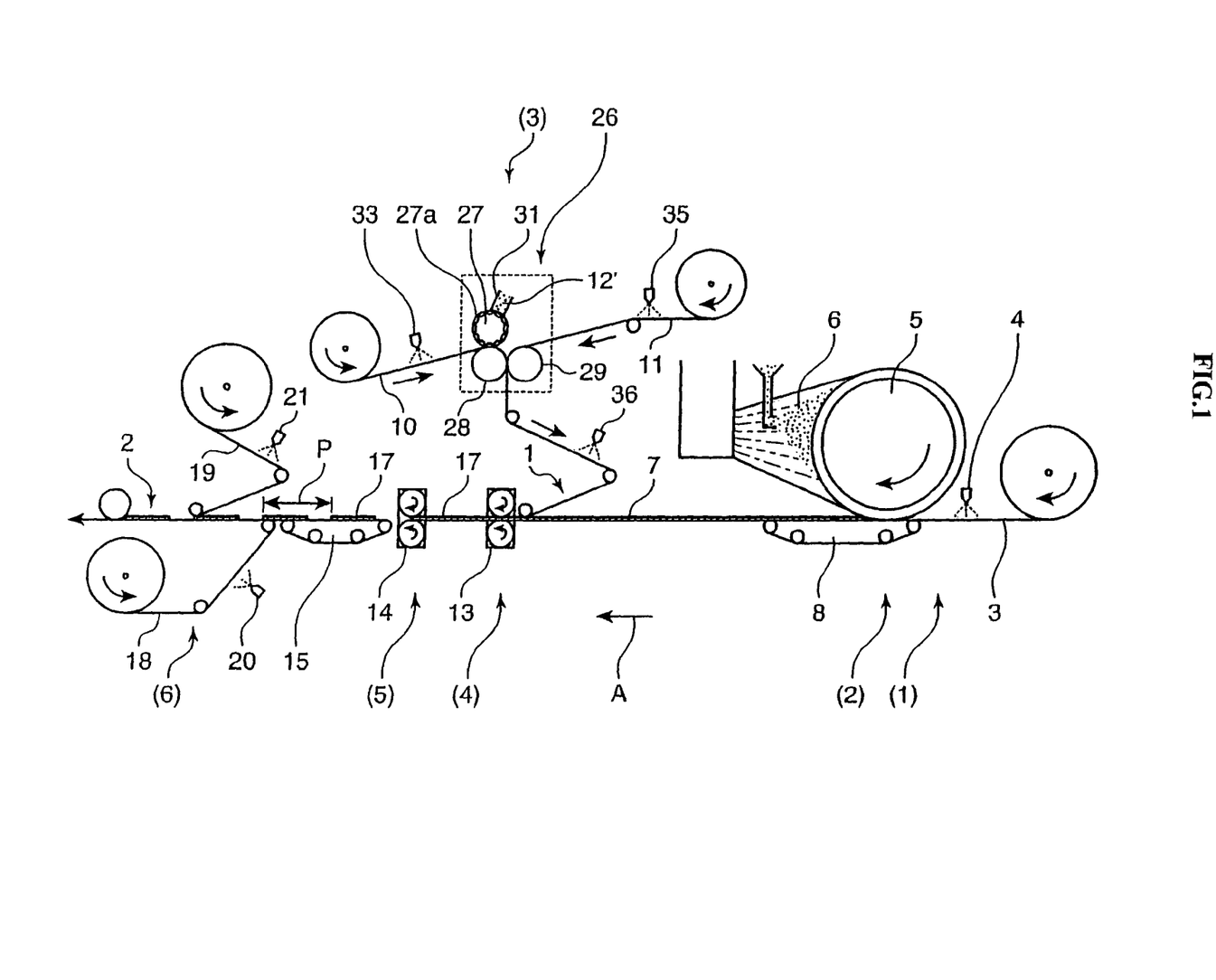
FIG. 1 is a system diagram that shows a manufacturing apparatus of a disposable absorbent article in which a manufacturing device of a sheet-shaped absorbent body is assembled.

FIG. 1 is a system drawing that shows a continuous manufacturing apparatus of a disposable absorbent article 2 (see FIG. 6) in which a manufacturing device of a sheet-shaped water-absorbent body 1 (see FIG. 5) is incorporated.

In the continuous manufacturing line of the disposable absorbent article 2, a carrier sheet 3 is drawn from a roll body on the right side of the Figure in the length direction (leftward) A so as to be continuously drawn out.

In process (1), a hot-melt bonding agent is applied to the upper face of the carrier sheet 3 by a hot-melt bonding-agent applying device 4.

In process (2), fibers 6 mixed with highly water-absorbent resin particles are blown to the circumferential face of a pattern drum 5 to be laminated thereon, and this laminated fiber aggregate 7 is continuously carried on the upper face of the carrier sheet 3 at the position of a suction conveyor 8 to be bonded thereon.

Figure 5A:
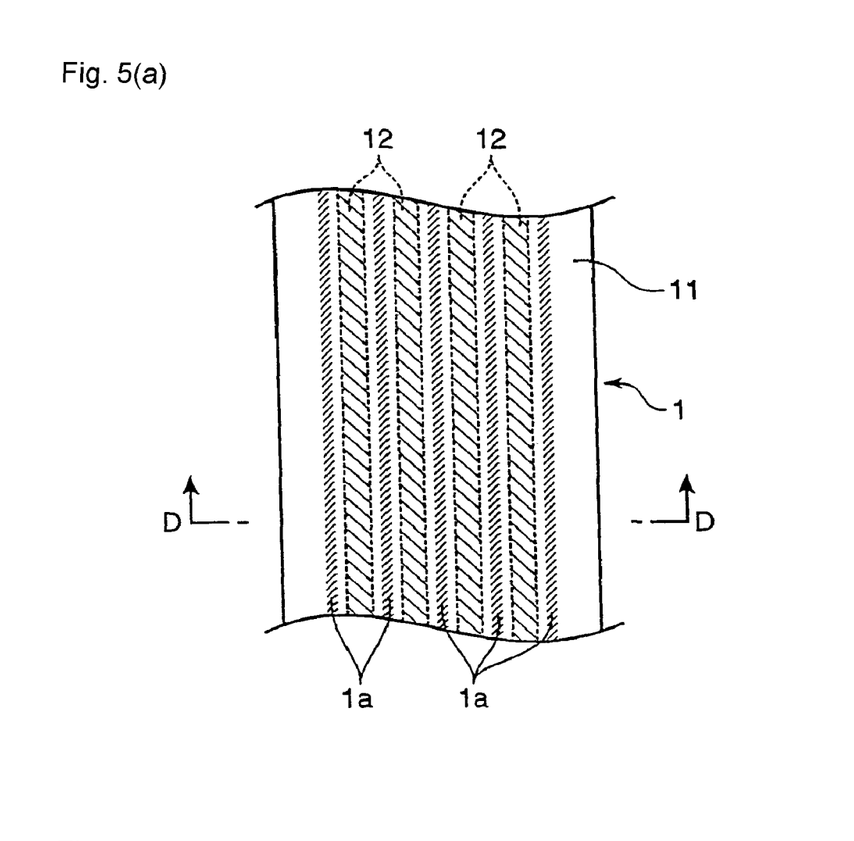
Figure 5B:
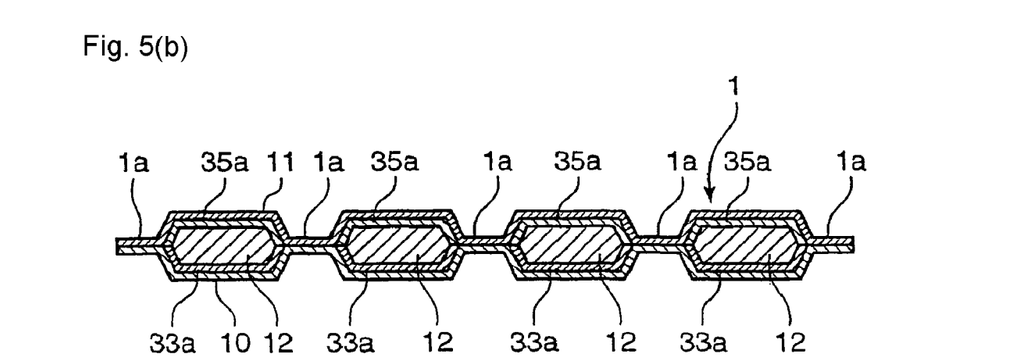

Process (3) is a process for continuously manufacturing the sheet-shaped water-absorbent body 1, which will be described later in detail, and in this process (3), as shown in FIG. 5, the sheet-shaped water-absorbent body 1 in which a highly water-absorbent resin particle layer 12 is intermittently sandwiched between a base sheet 10 and a covering sheet 11 in the width direction to be bonded into an integral form is continuously manufactured.

In process (4), the sheet-shaped water-absorbent body 1 with a lower face (facing the fiber aggregate 7) coated with a hot-melt bonding agent is contact-bonded by a press roller 13 with its lower face placed on the upper face of the fiber aggregate 7 to be bonded into an integral form; thus, an absorbent body 17 is continuously manufactured.

In process (5), the absorbent body 17 is cut into a predetermined length by a mat cutter 14, and then carried on a transport conveyor 15 having a high speed to be shifted while being adjusted to a pitch P for each single article of disposable absorbent articles 2.

In process (6), a hot-melt bonding agent is applied to an inner face of a liquid-impermeable back sheet 18 drawn from the roll body by a hot-melt bonding agent applying device 20, and the absorbent body 17 is intermittently placed on the inner face of this back sheet 18, and bonded thereto.

In addition, a hot-melt bonding agent is applied to the inner face of a liquid-permeable top sheet 19 drawn from a roll body by a hot-melt bonding agent applying device 21, and the inner face of the back sheet 21 (face facing the absorbent body 17) is placed on the upper face of the absorbent body 17 so that the absorbent body 17 is sandwiched between the back sheet 18 and the top sheet 19 to be bonded into an integral form; thus, a disposable absorbent article 2 can be continuously manufactured.

Although the succeeding processes are not shown in Figures, the back sheet 18 and the top sheet 19 are cut for each single article of disposable absorbent articles 2, and each article is double-folded or triple-folded in the length direction to be made compacter; thus, the resulting articles are packaged for each of predetermined number thereof.

In the continuous manufacturing apparatus of the disposable absorbent articles 2 of FIG. 1, the absorbent body 17 is manufactured by combining the sheet-shaped water-absorbent body 1 and the fiber aggregate 7; however, the absorbent body 17 may be formed by using only the sheet-shaped water-absorbent body 1, without using the fiber aggregate 7.

In addition, the manufacturing device of the sheet-shaped water-absorbent body 1 is incorporated into the continuous manufacturing apparatus of the disposable absorbent article 2; however, the manufacturing apparatus of the disposable absorbent article 2 and the manufacturing device of the sheet-shaped water-absorbent body 1 may be installed in places (factories) separated from each other. In this case, the sheet-shaped water-absorbent body 1 is supplied as a roll body in process (4).

Figures 2A, 2B:
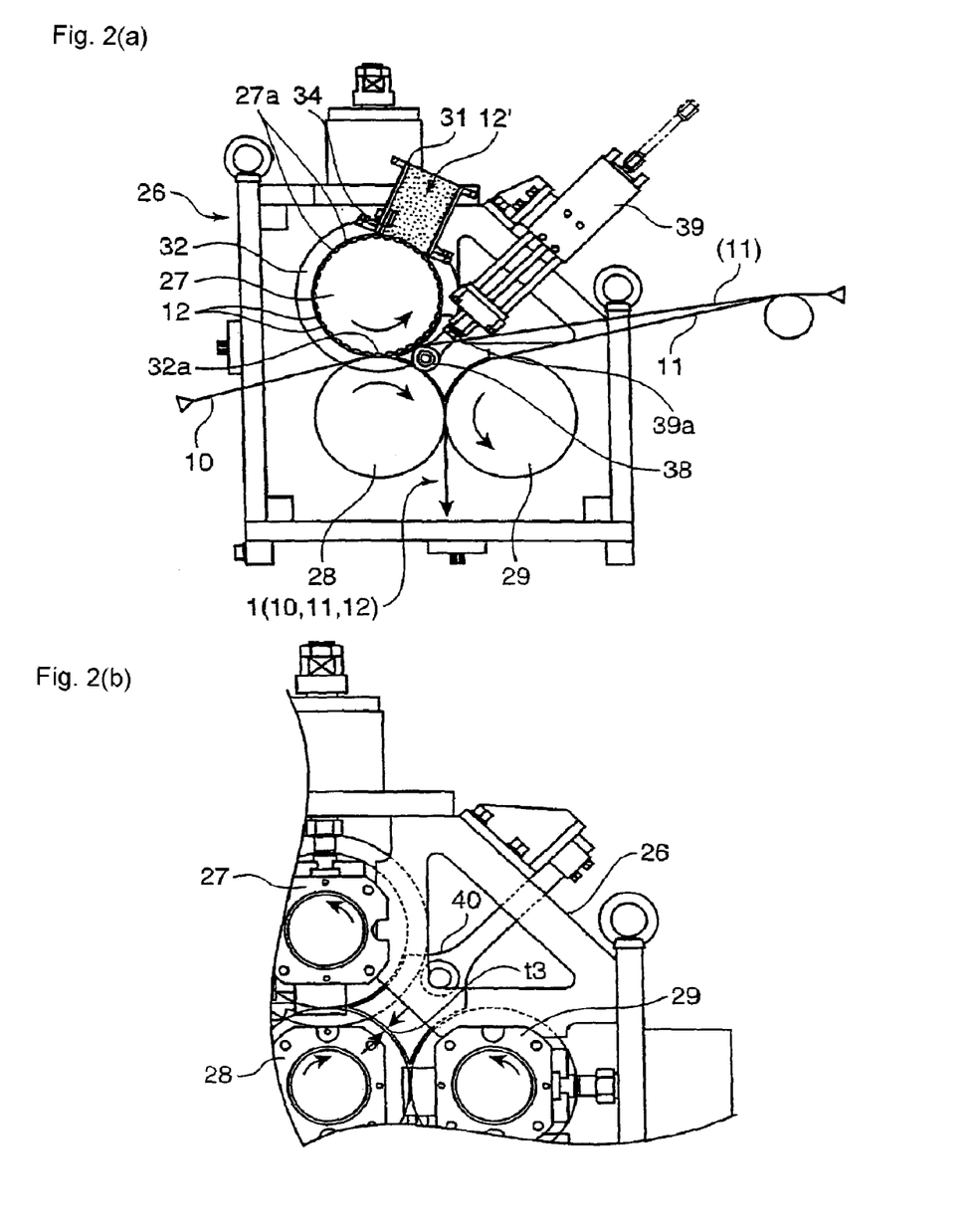

Referring to FIG. 2(*a*), the following description will discuss process (3) for manufacturing the sheet-shaped water-absorbent body 1 in detail.

The manufacturing device of the sheet-shaped water-absorbent body 1, which is incorporated in a frame member 26, has a structure in which: a temporary receiving roller 27 is attached to the upper portion of this frame member 26; a receiving and transferring roller 28 is attached to the lower portion thereof; and a contact-bond fixing roller 29 is attached to the right side thereof, with the temporary receiving roller 27 and the receiving and transferring roller 28 being made close to each other vertically, as well as with the receiving and transferring roller 28 and the contact-bond fixing roller 29 being made close to each other horizontally. The distance between the temporary receiving roller 27 and the receiving and transferring roller 28 is preferably set to 3 mm or less, more preferably, to 1 mm.

The temporary receiving roller 27 is rotated counterclockwise, the receiving and transferring roller 28 is rotated clockwise, and the contact-bond fixing roller 29 is rotated counterclockwise, and in this arrangement, the respective surface peripheral velocities are set to the same speed, or the temporary receiving roller 27 is set to a slightly lower velocity. In other words, the respective rollers 27 to 29 are basically set to the same peripheral velocity; however, with respect to the temporary receiving roller 27, its surface peripheral velocity is variably determined so as to be set to a surface velocity slightly lower than that of the other rollers 28 and 29. The reason for this will be described later.

As shown in the front view of FIG. 3(*a*), rows of a plurality of concave grooves (four in this example) 27a, which extend along the circumference of the roller face with a predetermined interval t1 in the roller length direction, are formed in the roller surface of the temporary receiving roller 27, and as shown in the side sectional view showing an essential portion of FIG. 3(*b*), each of the concave grooves 27a is formed so as to have intermittent portions (cells) with a predetermined interval t2 along the circumference of the roller face (rotation shifting direction). Each concave groove 27a has a bottom face 27b formed into an arc shape along the circumference of the roller face.

Figure 3A:
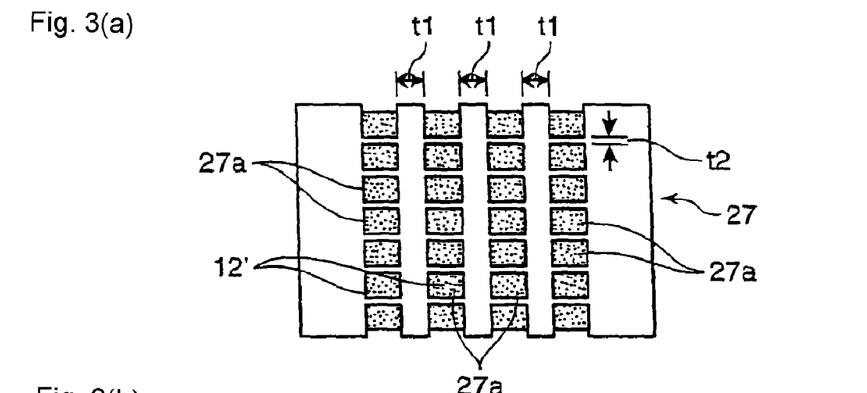
Figure 3B:
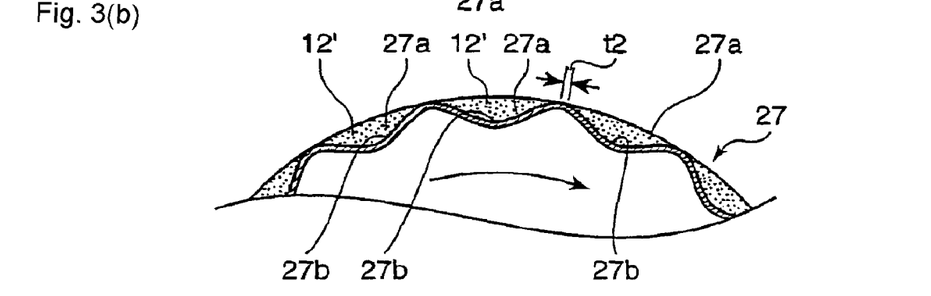
Figure 3C:
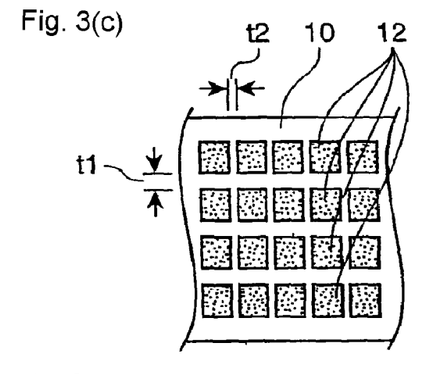
Figure 3D:
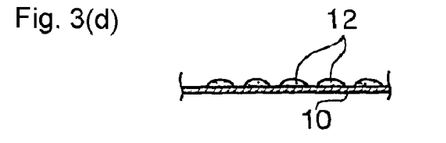

Each concave groove 27a is used for receiving highly water-absorbent resin particles 12' and for shifting these while being held in a layer state. Here, when concave grooves having the same pattern as the temporary receiving roller 27 are also formed on the roller face of the receiving and transferring roller 28, the highly water-absorbent resin particles 12' can be stably transferred so that it is possible to prevent the resin particles from scattering on the periphery.

A box 31 that supplies the highly water-absorbent resin particles 12' to each of the concave grooves 27a of the roller face is placed above the temporary receiving roller 27, and an arc-shaped guide member 32, used for holding the highly water-absorbent resin particle layer 12 that has been supplied to each of the concave grooves 27a and formed into a layer, is installed in a manner so as to face the roller face of the temporary receiving roller 27 located from the box 31 to the roller face of the receiving and transferring roller 28. Here, a tank that stores the highly water-absorbent resin particles 12' may be connected to the upper portion of the box 31.

The gap between the temporary receiving roller 27 and the guide member 32 is preferably set to 1 mm or less, more preferably, to 0.2 mm or less. The temporary receiving roller 27 and the guide member 32 are preferably made of a metal material having high hardness. Since the highly water-absorbent resin particles 12' are always made in contact with these, these members are subjected to severe abrasion. With respect to the metal material of the temporary receiving roller 27, SKH51 having hardness in a range of HRC61±1 is preferably used, and with respect to the metal material of the guide member 32, SKH51 having hardness in a range of HRC63±1 is preferably used.

The base sheet 10, which has been drawn from a roll body in the length direction so as to be continuously shifted, has its upper face (inner face) coated with a hot-melt bonding agent by a hot-melt bonding agent applying device 33 (see FIG. 1), and is then directed downward with its lower face (outer face) being made in contact with the roller face of the receiving and transferring roller 28 from the left side so as to be wound around the roller face of the receiving and transferring roller 28. In other words, the base sheet 10 is shifted in a held (wrapped) state on the roller face of the receiving and transferring roller 28.

The highly water-absorbent resin particles 12' are supplied from the box 31 to each of the concave grooves 27a of the roller face of the temporary receiving roller 27. At this time, since a scraping member 34 is attached to a wall portion on the downstream side in the rotation direction inside the box 31, the excessive portion of the highly water-absorbent resin particles 12' beyond the capacity of each of the concave grooves 27a is scraped off so that a fixed amount of the highly water-absorbent resin particles 12' corresponding to the amount that just makes full of each of the concave grooves 27a is received.

The highly water-absorbent resin particle layer 12 that has been received by each of the concave grooves 27a to be formed into a layer, is shifted directly above the base sheet 10 wrapped on the roller face of the receiving and transferring roller 28, while being held inside each of the concave grooves 27a by the guide member 32, so that simultaneously with the coming off from the end 32a of the guide member 32, it is transferred onto the upper face of the base sheet 10 coated with the hot-melt bonding agent. In other words, the highly water-absorbent resin particle layer 12 is shifted in a held state on the roller face of the temporary receiving roller 27.

Immediately after the transferring process, the highly water-absorbent resin particle layer 12 forms a square shape, with its distances t1 and t2 being kept vertically as well as laterally, as shown in FIGS. 3(*c*) and 3(*d*), and in this case, when the interval t2 is made narrower, as shown in FIGS. 3(*e*) and 3(*f*), it is allowed to form a linear shape in the shifting direction of the base sheet 10 with the interval t1 being intermittently kept in the width direction in the course of the shift.

Figure 4A:
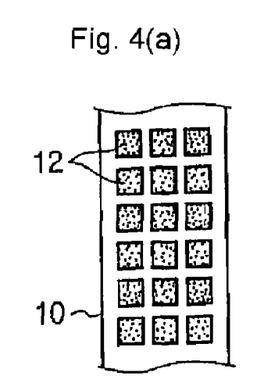
Figure 4B:
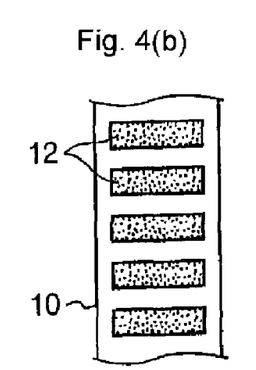

In FIGS. 3(a) and 3(b), since the square-shaped concave grooves 27a are placed vertically as well as horizontally, the highly water-absorbent resin particle layer 12 forms a square shape immediately after the transferring process, as shown in FIG. 4(a) for use in comparison; however, when concave grooves 27a, each having a laterally elongated rectangular shape, are placed in the vertical direction, the highly water-absorbent resin particle layer 12 is allowed to form a laterally elongated rectangular shape as shown in FIG. 4(b) immediately after the transferring process.

Figure 4C:
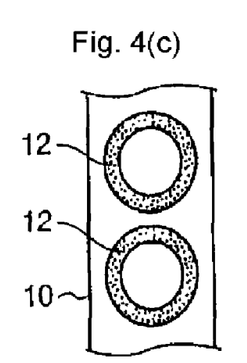
Figure 4D:
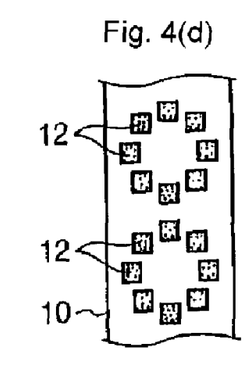
Figure 4E:
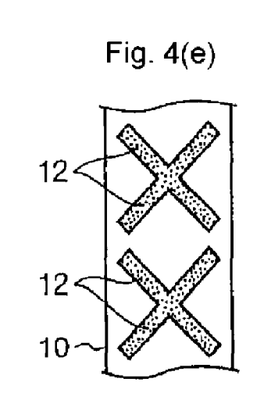
Figure 4F:
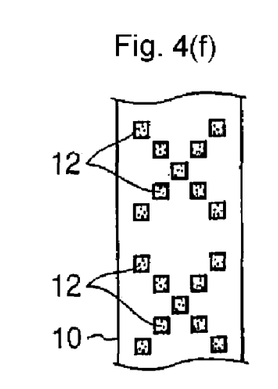

In the same manner, as shown in FIG. 4(c), when each of the concave grooves 27a is formed into a ring shape, the highly water-absorbent resin particle layer 12 is also made into the same shape; as shown in FIG. 4(d), when concave grooves 27a, each having a square shape, are combined into a ring shape, the highly water-absorbent resin particle layer 12 is also made into the same shape; as shown in FIG. 4(e), when concave grooves 27a are formed into an X-shape, the highly water-absorbent resin particle layer 12 is also made into the same shape; and as shown in FIG. 4(f), when concave grooves 27a, each having a square shape, are combined into an X-shape, the highly water-absorbent resin article layer 12 is also made into the same shape. Although not shown in Figures, each of the concave grooves 27a may be made into a lozenge or an elliptical shape, and the concave grooves 27a may be arranged in a snaking format around the roller circumferential face (rotation shifting direction).

In this manner, it is possible to form highly water-absorbent resin particle layers 12 having various patterns by appropriately selecting the shape of the concave grooves 27a.

Figure 3E:
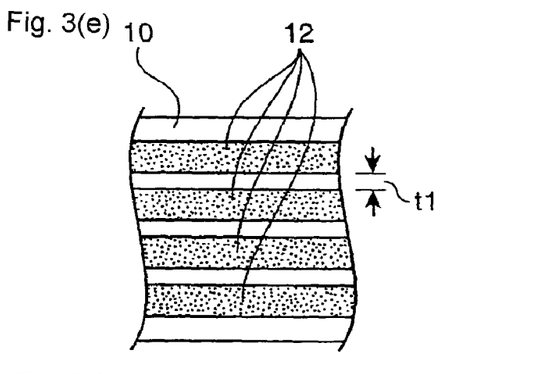
Figure 3F:
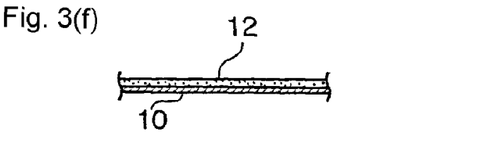
Figure 4G:
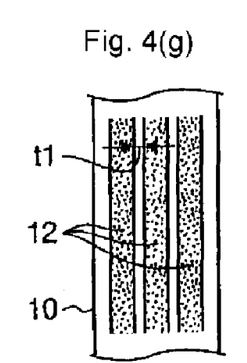
Figure 4H:
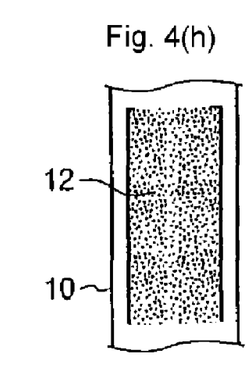

As described above, in the case when the interval t2 is made narrower, the highly water-absorbent resin particle layer 12 is formed into a linear shape in the shifting direction of the base sheet 10 with an interval t1 being intermittently kept in the width direction in the course of a shift as shown in FIGS. 3(e) and 3(f), and with respect to the temporary receiving roller 27, by setting the surface peripheral velocity to a level slightly slower than that of the other rollers 28 and 29, the highly water-absorbent resin particle layer 12 is formed into a linear shape in the shifting direction of the base sheet 10 with an interval t1 being intermittently kept in the width direction as shown in FIG. 4(g) in the example of FIG. 4(a), in the same manner as FIGS. 3(e) and 3(f); and, in the example of FIG. 4(b), it is also formed into a linear shape in the shifting direction of the base sheet 10, as shown in FIG. 4(h). Here, with respect to cases shown in FIGS. 4(c), 4(d), 4(e) and 4(f) as well, it is possible to provide a pattern that is blurred in the shifting direction. Here, the amount of the highly water-absorbent resin particles 12' to be transferred onto the base sheet 10 is determined by the capacity of each of the concave grooves 27a so that by adjusting the capacity of the concave groove 27a, the degree of the blurred state in the shifting direction of a pattern can be changed.

The covering sheet 11, drawn from a roll body so as to be continuously shifted, has its upper face (inner face) coated with a hot-melt bonding agent by a hot-melt bonding agent applying device 35 (see FIG. 1), and is then wound around the roller face of the contact-bond fixing roller 29 in a manner so as to be drawn downward with its lower face (outer face) being made in contact with the roller face of the contact-bond fixing roller 29 from the right side. In other words, the covering sheet 11 is shifted in the held (wrapped) state around the roller face of the contact-bond fixing roller 29.

Then, the base sheet 10 on which the highly water-absorbent resin particle layer 12 has been transferred and the covering sheet 11 are joined between the receiving and transferring roller 28 and the contact-bond fixing roller 29 so that a sheet-shaped water-absorbent body 1 in which the highly water-absorbent resin particle layer 12 is sandwiched between the base sheet 10 and the covering sheet 11 by the contact bonding process of the contact-bond fixing roller 29 to be bonded into an integral form is continuously manufactured.

The sheet-shaped water-absorbent body 1 thus continuously manufactured has its lower face (facing the fiber aggregate 7) coated with a hot-melt bonding agent by a hot-melt bonding agent applying device 36 (see FIG. 1) as explained in process (4), and is then placed on the upper face of the fiber aggregate 7.

The contact-bond fixing roller 29, which forms a heat roller, has a structure in which a step portion is formed on the roller face of the contact-bond fixing roller 29 so that the two ends of the base sheet 10 and the covering sheet 11 are melt-bonded, with the adjacent highly water-absorbent resin particle layers 12 being also melt-bonded to each other; thus, as shown in FIG. 5(b), a sealing portion 1a is formed on the sheet-shaped water-absorbent body 1. Here, the receiving and transferring roller 28 is also preferably prepared as a heat roller.

The base sheet 10 on which the highly water-absorbent resin particle layer 12 is preferably joined to the covering sheet 11 as soon as possible to be bonded into an integral form so that the highly water-absorbent resin particle layer 12 is desirably fixed at a predetermined position quickly in a stable manner.

For this reason, as shown in FIG. 2(a), a press contact roller 38, used for pressing the covering sheet 11 onto the base sheet 10 on the receiving and transferring roller 28, is preferably installed at a position prior to the contact-bond fixing roller 29 between the temporary receiving roller 27 and the contact-bond fixing roller 29. This press contact roller 38 is supported by a piston rod 39a of a hydraulic cylinder (or an air-pressure cylinder may be used; hereinafter, the same is true) 39, and the covering sheet [reference numeral (11)] is wound around the press contact roller 38, and immediately after having been released between the temporary receiving roller 27 and the receiving and transferring roller 28, the covering sheet 11 is pressed onto the base sheet 10 on which the highly water-absorbent resin particle layer 12 has been transferred, to cover thereon. Thereafter, by the contact bonding process of the contact-bond fixing roller 29, the highly water-absorbent resin particle layer 12 is sandwiched between the base sheet 10 and the covering sheet 11, and bonded into an integral form. Here, the press contact roller 38 is adjusted in its press-contacting force by the hydraulic cylinder 39 so that with respect to the highly water-absorbent resin particle layer 12 to be transferred onto the upper face of the base sheet 10, the thickness thereof, which is varied depending on the amount of the highly water-absorbent resin particle layer 12, is properly adjusted. Here, the step portion to form the sealing portion 1a may be formed on the roller face of the press contact roller 38 instead of being formed on the contact-bond fixing roller 29. The press contact roller 38 is preferably designed to have a diameter of about 14 mm.

As shown in FIG. 2(b), in place of the press contact roller 38, an arc-shaped protective plate member 40, which is located close to the roller face of the receiving and transferring roller 28 with a predetermined interval t3, may be installed.

This protective plate member 40 is used for preventing the highly water-absorbent resin particle layer 12 from flowing during a period from the transferring process of the highly water-absorbent resin particle layer 12 onto the base sheet 10 until the press contacting and fixing processes of the covering sheet 11 thereon by using the contact-bond fixing roller 29. The distance t3 between the roller face of the receiving and transferring roller 28 and the protective plate member 40 is preferably set in a range from 0.5 to 5 mm.

By the use of this protective plate member 40, it becomes possible to obtain a sheet-shaped water-absorbent body 1 with the sheet being stably fixed on a predetermined position. When the above-mentioned distance t3 is less than 0.5 mm, the distance is too narrow, with the result that the highly water-absorbent resin particles 12' tend to clog or the hot-melt bonding agent on the inner face (upper face) of the base sheet 10 tends to adhere to the protective plate member 40 making it difficult to carry out controlling processes; in contrast, when it exceeds 5 mm, it becomes impossible to achieve the objective of preventing the highly water-absorbent resin particle layer 12 from flowing.

FIG. 5 show a sheet-shaped water-absorbent body 1 continuously manufactured in the above-mentioned process (3), and FIG. 5(a) is a plan view thereof, and FIG. 5(b) is an enlarged sectional view taken along line D-D of FIG. 5(a).

The sheet-shaped water-absorbent body 1 has a structure in which the highly water-absorbent resin particle layer 12 is sandwiched between the base sheet 10 and the covering sheet 11 and bonded into an integral form, with the sealing portions 1a being formed between the adjacent highly water-absorbent resin particle layers 12. Here, reference numeral 33a represents a hot-melt bonding agent layer that is applied onto the base sheet 10 by a hot-melt bonding agent applying device 33, and reference numeral 35a represents a hot-melt bonding agent layer applied onto the covering sheet 11 by a hot-melt bonding agent applying device 35.

The base sheet 10 and the covering sheet 11 are preferably formed by liquid-permeable non-woven fabric materials. Examples of the non-woven fabric materials include: hydrophilic fibers (cotton, rayon, cellulose, etc.), fibers prepared by subjecting hydrophobic fibers (polyethylene, polypropylene, polyethylene terephthalate, nylon, polyamide, etc.) to a hydrophilic-property applying treatment by using a surfactant or the like, and mixed fibers of these fibers.

The highly water-absorbent resin particle layer 12 is formed by using conventionally known highly water-absorbent resin particles utilized as disposable absorbent articles, such as polyacrylic-acid salt based, cellulose-based, starch-based, polyacrylonitrile-based, polyamide-based and polyamino-acid-based particles. The particle size is preferably set to a size from 37 to 1000 mm, in particular, from 150 to 700 mm, in particles of 90% by mass or more of the entire mass.

With respect to the hot-melt bonding agent, conventionally known hot-melt bonding agents, such as olefin-based, rubber-based and EVA-based hot-melt bonding agents, may be utilized, and among these, rubber-based hot-melt bonding agents, which have superior flexibility, are preferably used. With respect to the coating method, conventionally known coating methods, such as coater-coating, beads-coating, spiral-coating, melt-blow-coating and omega-coating methods, may be utilized, and among these, the spiral-coating method is preferably used for a hot-melt bonding agent to be applied to the base sheet 10, since this method hardly intervenes with the absorbing speed, while the melt-blow-coating method is also preferably used for a hot-melt bonding agent to be applied to the covering sheet 11, since this method improves the fixing stability.

The fiber aggregate 7 forms an absorbing body that is normally used as a disposable absorbent article in which highly absorbent resin particles are mixed in hydrophilic fibers (mainly, pulverized pulp fibers) and formed into a predetermined shape, and covered with tissue paper or liquid-permeable non-woven fabric.

Figure 6A:
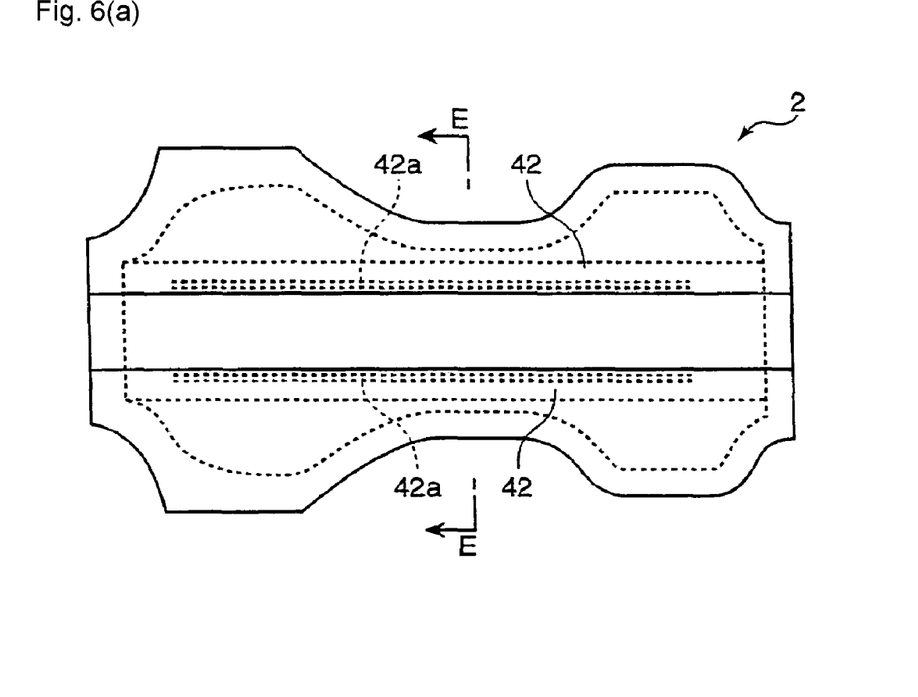
Figure 6B:
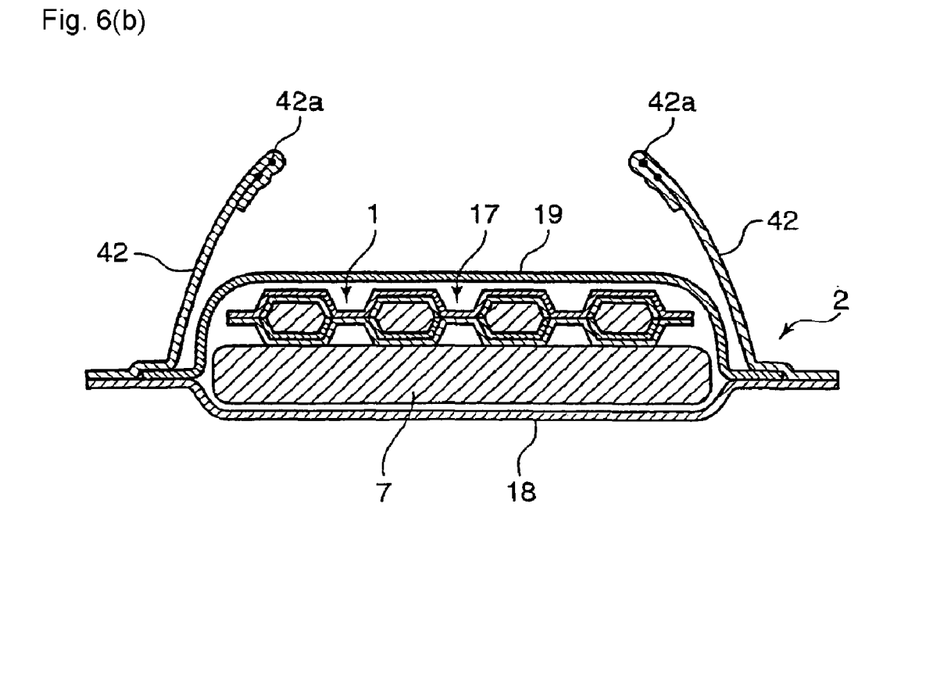

FIG. 6 show a disposable absorbent article 2 that is continuously manufactured in the above-mentioned process (5); and FIG. 6(a) is a plan view and FIG. 6(b) is an enlarged sectional view taken along line E-E of FIG. 6(a).

The disposable absorbent article 2 has a urine-absorbing pad type in which the absorbent body 17 is sandwiched between a back sheet 18 and a top sheet 19 and bonded into an integral form, and on both sides of the disposable absorbent article 2, rising flaps 42, each having an adjacent elastic member 42a, may be placed. In addition, the disposable absorbent article 2 may have a shape such as a gourd shape so as to be well fitted to a wearer's body form.

In addition, a tape-type disposable absorbent article with a fastening tape or a shorts-type disposable absorbent article in which expansion elastic members are formed along a waist opening portion and right and left two leg openings may be used.

The back sheet 18 is preferably formed by a liquid-impermeable film material, a water-repellent non-woven fabric material or a composite material of these, and the top sheet 19 is preferably formed by a liquid-permeable non-woven fabric material.

The rising flaps 42 are preferably formed by a water-repellent non-woven fabric material.

With respect to the above-mentioned elastic member 42a, conventionally-known elastic materials utilized as disposable absorbent articles, such as polyurethane threads, polyurethane films and natural rubber, may be used.

In the case when the above-mentioned manufacturing device of the sheet-shaped water-absorbent body 1 is used, the receiving and transferring roller 28 that transfers the base sheet 10 which is being held on its roller face, the temporary receiving roller 27 that transfers the highly water-absorbent resin particle layer 12 on the base sheet 10 while shifting it in a held state on its roller face, and a contact-bond fixing roller 29 that bonds the base sheet 10, the highly water-absorbent resin particle layer 12 and the covering sheet 11 into an integral form while shifting the covering sheet 11 in a held state on its roller face are installed so that the highly water-absorbent resin particle layer 12 is transferred on the base sheet 10, while being shifted in the held state on its roller face; therefore, it becomes possible to prevent the highly water-absorbent powder particles 12' from bouncing, which makes this device different from the system in which highly water-absorbent powder particles 12' are allowed to naturally drop to form a layer, and consequently to prepare the sheet-shaped water-absorbent body 1 in which the highly water-absorbent resin particle layer 12 is stably fixed onto a predetermined position.

In addition, since the base sheet 10, the highly water-absorbent resin particle layer 12 and the covering sheet 11 are bonded into an integral form while being shifted in the respective held states on roller faces, the shifting speeds and the bonding processes of the respective materials 10 to 12 can be easily controlled, and the processes can also be carried out even in a narrow space; therefore, the manufacturing device is easily assembled into a continuous manufacturing line of the disposable absorbent article 2

Furthermore, in the arrangement in which the surface peripheral velocities of the receiving and transferring roller 28, the temporary receiving roller 27 and the contact-bond fixing roller 29 are set to the same speed, since the respective materials 10 to 12 that are shifted in the held states on the respective rollers 27 to 29 are shifted at the same speed, it becomes difficult for the highly water-absorbent resin particle layer 12 to flow so that the sheet-shaped water-absorbent body 1 in which the powder particle layer is stably fixed at a predetermined position can be obtained, and it becomes possible to easily carry out the controlling process. In particular, in the case when the manufacturing device of the sheet-shaped water-absorbent body 1, which has been incorporated into the manufacturing apparatus of the disposable absorbent article 2, is used, the manufacturing apparatus of the disposable absorbent article 2 tends to be fluctuated in its manufacturing speed due to influences of factors other than the sheet-shaped water-absorbent body 1; therefore, by providing more parts that can be controlled at the same peripheral velocity, it becomes possible to carry out driving operations easily and also to stabilize the product quality.

In addition, since the water-absorbent resin particle layer 12 is transferred onto the base sheet 10 while being shifted in the same direction as the base sheet 10, the highly water-absorbent resin particle layer 12 can be smoothly transferred while preventing the highly water-absorbent resin particles 12' from bouncing.

Furthermore, since the covering sheet 11 can be bonded in a short time after the highly water-absorbent resin particle layer 12 has been transferred onto the base sheet 10, the highly water-absorbent resin particle layer 12 can be quickly sealed between two sheets 10 and 11 so that it becomes possible to obtain the sheet-shaped water-absorbent body 1 in which the resin particle layer is stably fixed at a predetermined position.

In addition, since the highly water-absorbent resin particles 12', which are received by the concave grooves 27a and held in a layer form, are transferred onto the base sheet 10, it becomes possible to prevent the highly water-absorbent resin particles 12' from bouncing, which makes this structure different from the system in which powder particles are allowed to naturally drop to form a layer; therefore, it becomes possible to prepare the sheet-shaped water-absorbent body 2 in which the highly water-absorbent resin particle layer 12 is stably fixed onto a predetermined position. Here, since the concave grooves 27a hold the highly water-absorbent resin particles 12' individually, it is possible to prevent the highly water-absorbent resin particles 12' from being spilled from the concave grooves 27a, even when the concave grooves 27a are directed laterally or upside down following the rotation of the temporary receiving roller 27, and consequently to prevent the resin particles from contaminating the periphery of the device.

In addition, upon transferring the highly water-absorbent resin particle layer 12 onto the base sheet 10, the total amount thereof can be transferred without a residual highly water-absorbent resin particle layer 12 in the bottom portion of each concave groove 27a.

Furthermore, the highly water-absorbent resin particle layer 12 can be transferred onto the base sheet 10, with the resin particle layer being enclosed inside the concave grooves 27a by sealing the receiving opening of the concave grooves 27a with the guide member 32 so that the highly water-absorbent resin particles 12' can be prevented from bouncing, which makes this system different from the system of forming a layer by utilizing natural drops; therefore, it becomes possible to obtain a sheet-shaped water-absorbent body 1 in which the highly water-absorbent resin particle layer 12 is stably fixed at a predetermined position. In addition, it is also possible to prevent the highly water-absorbent resin particles 12' from spilling out of the concave grooves 27a and consequently contaminating the periphery of the device.

Since the contact-bond fixing roller 29 is prepared as a heat roller (the receiving and transferring roller 28 may also be prepared as a heat roller), the sheets 10 and 11 can be partially melt-bonded to each other through heat, and it becomes unnecessary to install a heat roller separately; therefore, the device space is made compacter, making it possible to easily carry out the controlling operations, and consequently to easily assemble the manufacturing device of the sheet-shaped absorbent body is easily assembled into a continuous manufacturing line of the disposal absorbent article.

In addition, with the arrangement in which the press contact roller 38 is installed, immediately after having been transferred onto the base sheet 10, the resulting highly water-absorbent resin particle layer 12 is covered with the covering sheet 11 and subjected to a press-contacting process; therefore, it becomes possible to prevent the highly water-absorbent resin particle layer 12 from flowing, and consequently to obtain the sheet-shaped water-absorbent body 1 in which the resin particle layer is stably fixed at a predetermined position.

Furthermore, by assembling the above-mentioned manufacturing device of the sheet-shaped water-absorbent body 1 into the continuous manufacturing apparatus of the disposable absorbent article 2, it is possible to stably manufacture the disposable absorbent article 2 having the sheet-shaped water-absorbent body 1 in which the highly water-absorbent resin particle layer 12 is stably fixed to a predetermined position quickly, and also to manufacture the sheet-shaped water-absorbent body 1 through an in-line system; therefore, it becomes possible to provide the disposable absorbent article 2 having the sheet-shaped water-absorbent body 1 at a low price.

EXAMPLE 2

Figure 7A:
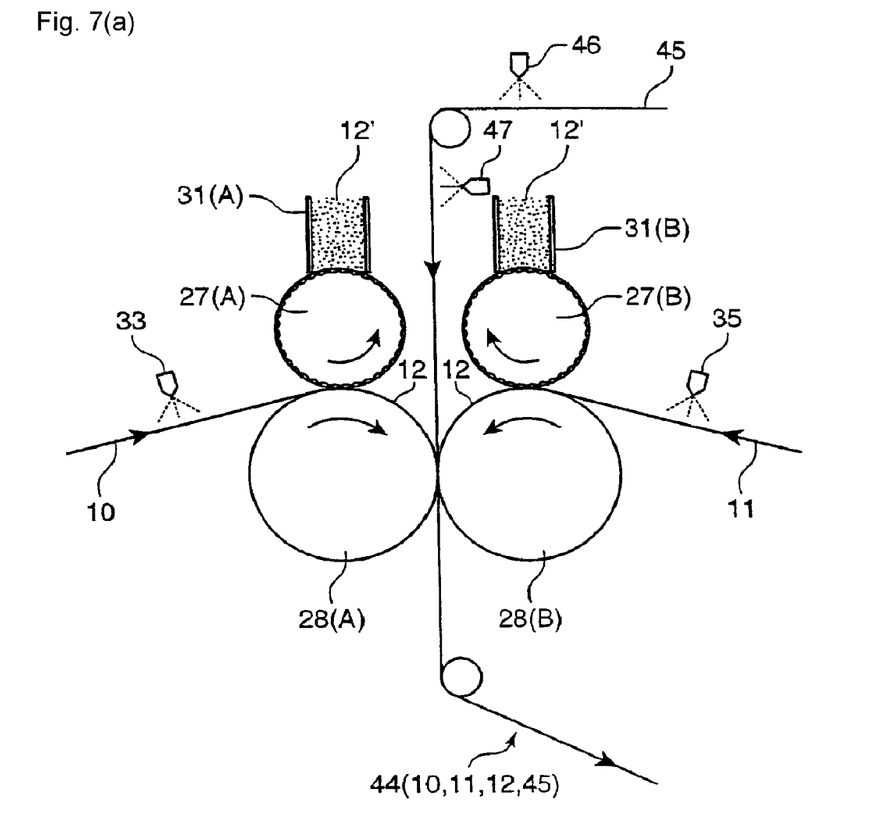
Figure 7B:
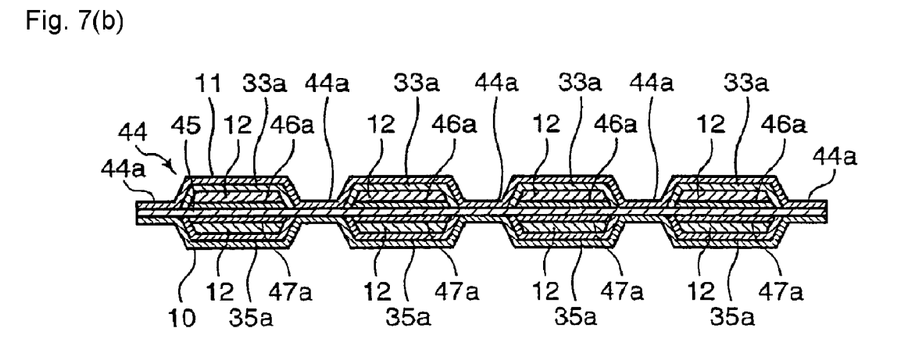

FIG. 7(a) shows a manufacturing device of a sheet-shaped water-absorbent body 44 composed of a plurality of layers, and FIG. 7(b) is a sectional view of the sheet-shaped water-absorbent body 44 composed of a plurality of layers.

As shown in FIG. 7(a), a base sheet 10 is coated with a hot-melt bonding agent or the like in its inner face by a hot-melt bonding-agent applying device 33, and then are held on a base-sheet side receiving and transferring roller 28(A), and highly water-absorbent resin particles 12', supplied from a base-sheet side box 31(A), are held on a base-sheet side temporary receiving roller 27(A) so that the resulting highly water-absorbent resin particle layer 12, formed into a layer state, is transferred onto the base sheet 10.

A covering sheet 11 is coated with a hot-melt bonding agent or the like in its inner face by a hot-melt bonding-agent applying device 35, and then are held on a coating-sheet side receiving and transferring roller 28(B), and highly water-absorbent resin particles 12', supplied from a coating-sheet side box 31(B), are held on a coating-sheet side temporary receiving roller 27(B) so that the resulting highly water-absorbent resin particle layer 12, formed into a layer state, is transferred onto the covering sheet 11.

An intermediate sheet 45 is interpolated between the base sheet 10 of the base-sheet side receiving and transferring roller 28(A) and the covering sheet 11 of the coating-sheet side receiving and transferring roller 28(B).

Hot-melt bonding agents are respectively applied to both of the faces of the intermediate sheet 45 by hot-melt bonding-agent applying devices 46 and 47 so that the intermediate sheet 45 is bonded to the base sheet 10 and the covering sheets 11 into an integral form between the base-sheet side receiving and transferring roller 28(A) and the coating-sheet side receiving and transferring roller 28(B); thus, a sheet-shaped water-absorbent body 44 composed of a plurality of layers is manufactured.

By using the above-mentioned manufacturing device, the base sheet 10, the intermediate sheet 45 and the covering sheet 11 can be melt-bonded to one another, as long as either the base-sheet side receiving and transferring roller 28(A) or the coating-sheet side receiving and transferring roller 28(B) is prepared as a heat roller.

In addition, by making the diameter of receiving and transferring rollers 28 (A, B) larger than that of temporary receiving rollers 27 (A, B), a space to which the intermediate sheet 45 is directed is prepared. In this case, in order to shift the respective materials 10, 11 and 45 at the same speed, it is necessary to rotate the receiving and transferring rollers 28 (A, B) slower than the temporary receiving rollers 27 (A, B).

In FIG. 7(b) that is a cross-sectional view of the sheet-shaped water-absorbent body 44 composed of a plurality of layers, when the highly water-absorbent resin particle layers 12 are placed at virtually the same position in upward and downward directions, the base sheet 10, the intermediate sheet 45 and the covering sheet 11 are melt-bonded to one another at one time to form a sealing portion 44a; however, the present invention is not intended to be limited to this layout. Here, reference numeral 46a represents a hot-melt bonding-agent layer applied on one surface of the intermediate sheet 45 by a hot-melt bonding-agent applying device 46, and reference numeral 47a represents a hot-melt bonding-agent layer applied on the other surface of the intermediate sheet 45 by a hot-melt bonding-agent applying device 47.

The intermediate sheet 45 is preferably formed by a liquid-permeable non-woven fabric material, and examples of the non-woven fabric material include: hydrophilic fibers (cotton, rayon, cellulose, etc.), fibers prepared by subjecting hydrophobic fibers (polyethylene, polypropylene, polyethylene terephthalate, nylon, polyamide, etc.) to a hydrophilic-property applying treatment by using a surfactant or the like, and mixed fibers of these fibers.

INDUSTRIAL APPLICABILITY

In accordance with the manufacturing method of a sheet-shaped body of the present invention, it becomes possible to stably fix a powder particle layer such as a highly absorbent resin particle layer at a predetermined position. In addition to an absorbent body of a disposable absorbent article, this sheet-shaped body can be used for various applications by changing the kinds of the powder particles.

The invention claimed is:

1. A method for manufacturing a sheet-shaped body in which a powder particle layer is sandwiched between a base sheet to which a bonding agent is applied and a covering sheet so as to be bonded into an integral body, comprising:
supplying powder particles from a source container into a concave groove of a face of a temporary receiving roller during rotation of the temporary receiving roller, wherein the supplied powder particles form the powder particle layer;
holding the powder particle layer onto the temporary receiving roller with a guide member extending over an arc length of the temporary receiving roller during rotation of the temporary receiving roller;
shifting the powder particle layer along a first path including a first path first portion encompassing an arc face portion of the temporary receiving roller;
shifting the base sheet along a second path including a second path first portion, wherein at the second path first portion the base sheet is moved between a receiving and transferring roller and the temporary receiving roller making contact with the powder particle layer on the temporary receiving roller,
transferring the powder particle layer onto the base sheet as the base sheet is moved to the second path first portion during rotation of both the receiving and transferring roller and the temporary receiving roller;
shifting the covering sheet along a third path while in a held state on a contact-bond fixing roller; and
bonding the base sheet, the powder particle layer and the covering sheet into an integral form on the third path during rotation of the contact-bond fixing roller; and
wherein the powder particle layer is shifted along the first path first portion at a shifting speed that is less than respective shifting speeds of the base sheet along the second path and the covering sheet along the third path, such that the powder particle layer transferred onto the base sheet is formed into a linear shape or a blurred pattern in a shifting direction.

2. The method for manufacturing the sheet-shaped body according to claim 1, wherein
the process for transferring the powder particle layer onto the base sheet includes shifting the powder particle layer in a same direction as the base sheet.

3. The method for manufacturing the sheet-shaped body according to claim 1,
wherein the base sheet is moved between the receiving and transferring roller and the contact-bond fixing roller at a second path second portion downstream of the second path first portion; and
wherein the base sheet, the powder particle layer and the covering sheet are bonded into the integral form in a region where the second path and third path overlap during rotation of both the receiving and transferring roller and the contact-bond fixing roller.

4. The method for manufacturing the sheet-shaped body according to claim 1, wherein
the powder particle layer is constituted by an absorbent resin particle layer.

5. A method for manufacturing a disposable absorbent article, comprising:
manufacturing a sheet-shaped body by the manufacturing method according to claim 4, sandwiching the sheet-shaped body between a liquid-permeable top sheet and a liquid-impermeable back sheet to and bonding the liquid-permeable top sheet, liquid-impermeable back sheet and the sheet-shaped body into an integral form so that the disposable absorbent article is produced.

6. The method for manufacturing the sheet-shaped body according to claim 1, wherein
the process for transferring the powder particle layer onto the base sheet and the process for bonding the covering sheet are carried out on the receiving and transferring roller face.

7. The method for manufacturing the sheet-shaped body according to claim 1, wherein
the process for transferring the powder particle layer onto the base sheet includes sealing an opening of the concave groove with the guide member such that the powder particle layer is enclosed inside the concave groove.

8. The method of claim 1, further comprising scraping with a scraping member excess powder particle capacity from a passing portion of the concave groove as the passing portion moves past the scraping member, wherein the scraping member is distinct from the guide member.

9. A method for manufacturing a sheet-shaped body in which a powder particle layer is sandwiched between a base sheet to which a bonding agent is applied and a covering sheet so as to be bonded into an integral body, comprising:

supplying powder particles from a source container into a concave groove of a face of a temporary receiving roller during rotation of the temporary receiving roller, wherein the supplied powder particles form the powder particle layer;

holding the powder particle layer onto the temporary receiving roller with a guide member extending over an arc length of the temporary receiving roller during rotation of the temporary receiving roller;

shifting the powder particle layer along a first path including a first path first portion encompassing an arc face portion of the temporary receiving roller;

shifting the base sheet along a second path including a second path first portion, wherein at the second path first portion the base sheet is moved between a receiving and transferring roller and the temporary receiving roller, transferring the powder particle layer onto the base sheet as the base sheet is moved to the second path first portion during rotation of both the receiving and transferring roller and the temporary receiving roller;

shifting the covering sheet along a third path while in a held state on a contact-bond fixing roller: and bonding the base sheet, the powder particle layer and the covering sheet into an integral form on the third path during rotation of the contact-bond fixing roller, a surface peripheral velocity of the temporary receiving roller being less than respective peripheral velocities of the contact-bond fixing roller and the receiving and transferring roller, such that the powder particle layer transferred onto the base sheet is formed into a linear shape or a blurred pattern in a shifting direction.

10. The method for manufacturing the sheet-shaped body according to claim 9, wherein the temporary receiving roller has a generally circular side profile.

11. A method for manufacturing a sheet-shaped body in which a powder particle layer is sandwiched between a base sheet to which a bonding agent is applied and a covering sheet so as to be bonded into an integral body, comprising:

shifting the base sheet along a second path including a second path first portion, wherein at the second path first portion the base sheet is moved between a receiving and transferring roller and the temporary receiving roller, supplying powder particles to at least one concave groove in a temporary receiving roller face of a temporary receiving roller facing said receiving and transfer roller, said powder particles being shifted while being held in a layer state as a powder particle layer within said at least one groove by rotation of said temporary receiving roller in a direction opposite to said receiving and transferring roller;

holding the powder particle layer onto the temporary receiving roller with a guide member extending over an arc length of the temporary receiving roller during rotation of the temporary receiving roller;

shifting the powder particle layer along a first path including a first path first portion encompassing an arc face portion of the temporary receiving roller;

transferring the powder particle layer held in said at least one groove onto the base sheet as the base sheet is moved to the second path first portion during rotation of both the receiving and transferring roller and the temporary receiving roller;

shifting the covering sheet along a third path while in a held state on a contact-bond fixing roller; and bonding the base sheet, the powder particle layer and the covering sheet into an integral form on the third path during rotation of the contact-bond fixing roller in a direction opposite to rotation of said receiving and transferring roller, a surface peripheral rotational velocity of the temporary receiving roller being less than respective surface peripheral velocities of the contact-bond fixing roller and the receiving and transferring roller such that the powder particle layer transferred onto the base sheet is formed into a linear shape or a blurred pattern in a direction of shifting of the base sheet.

12. A method for manufacturing a sheet-shaped body in which a powder particle layer having a first thickness is sandwiched between a base sheet to which a bonding agent is applied and a covering sheet so as to be bonded into an integral body, comprising:

rotating in a first direction a receiving and transferring roller that is located adjacent to each of a temporary receiving roller, a press contact roller, and a contact-bond fixing roller, wherein a first contact region occurs where the receiving and transferring roller is in nearest adjacency to the temporary receiving roller, a second contact region occurs where the receiving and transferring roller is in nearest adjacency to the press contact roller, and a bonding region occurs where the receiving and transferring roller is in nearest adjacency to the contact-bond fixing roller;

rotating the temporary receiving roller in a second direction opposite the first direction;

rotating the press contact roller in the second direction;

rotating the contact-bond fixing roller in the second direction;

receiving powder particles into a concave groove of a face of the temporary receiving roller during rotation of the temporary receiving roller, wherein the supplied powder particles form the powder particle layer;

holding the supplied powder particles onto the temporary receiving roller with a guide member extending over an arc length of the temporary receiving roller during rotation of the temporary receiving roller as the powder particle layer is moved into the first contact region;

shifting the base sheet along a first path, encompassing in order the first contact region, second contact region, and bonding region, wherein at least from the first contact region to the second contact region and then to the bonding region, the base sheet conforms to a shape of a face of the receiving and transferring roller;

transferring the supplied powder particles from the temporary receiving roller layer onto the base sheet while the base sheet and supplied powder particles are in the first contact region, wherein said receiving and transferring roller and said temporary receiving roller have a closest spacing in the first contact region that allows the base sheet on the receiving and transferring roller to make contact with the powder particle layer that is still on the temporary receiving roller;

shifting the covering sheet along a third path, encompassing in order said second contact region and said bonding region; and press contacting the covering sheet to the base sheet and powder particle layer in the second contact region, wherein said receiving and transferring roller and said press contact roller have a closest spacing in the second contact region that allows the base sheet with transferred powder particle layer on the receiving and transferring roller to make contact with a portion of the covering sheet having a shape conforming to a shape of a face of the press contact layer; and bonding the base sheet, the powder particle layer and the covering sheet into an integral form in the bonding region, wherein said receiving and transferring roller and said contact-bond fixing roller have a closest spacing in the bonding region that allows the base sheet, transferred powder particle layer, and covering sheet to be pressed between the contact-bond fixing roller and the receiving and transferring roller to form said integral form;

wherein the powder particle layer is moved by the temporary receiving roller into the first contact region at a shifting speed that is less than respective shifting speeds of the base sheet by the receiving and transferring roller and the covering sheet along the third path, such that the powder particle layer transferred onto the base sheet is formed into a linear shape or a blurred pattern in a shifting direction.

\* \* \* \* \*